US00PP34545P2

(12) United States Plant Patent
Couturieux

(10) Patent No.: US PP34,545 P2
(45) Date of Patent: Sep. 6, 2022

(54) ***HYDRANGEA* PLANT NAMED 'COUHARIE'**

(50) Latin Name: *Hydrangea paniculata*
Varietal Denomination: 'COUHARIE'

(71) Applicant: Jacques Couturieux, Moyenmoutier (FR)

(72) Inventor: Jacques Couturieux, Moyenmoutier (FR)

( * ) Notice: Subject to any disclaimer, the term of this patent is extended or adjusted under 35 U.S.C. 154(b) by 0 days.

(21) Appl. No.: 17/529,976

(22) Filed: Nov. 18, 2021

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Hydrangea* plant named 'COUHARIE' particularly distinguished by having early flowering and a short plant height, is disclosed.

3 Drawing Sheets

Genus and species: *Hydrangea paniculata.*
Variety denomination: 'COUHARIE'.

BACKGROUND OF THE NEW PLANT

The present invention comprises a new and distinct variety of *Hydrangea* plant, botanically known as *Hydrangea paniculata*, and hereinafter referred to by the variety name 'COUHARIE'. 'COUHARIE' originated from an open pollination in March 2011 using an unknown female *Hydrangea paniculata* parent and an unknown male *Hydrangea paniculata* parent. Seeds from the open-pollination were taken from the female parent and sown and a single plant was chosen in 2013.

'COUHARIE' was first propagated in June 2013 in France. 'COUHARIE' was found to reproduce true to type in successive generations of asexual propagation via softwood cuttings.

SUMMARY

The following are the most outstanding and distinguishing characteristics of this new variety when grown under normal horticultural practices in Boskoop, The Netherlands.

1. Early flowering; and
2. Short height of the plant.

DESCRIPTION OF THE PHOTOGRAPHS

This new *Hydrangea* plant is illustrated by the accompanying photographs which shows the plant's overall plant habit including form, and foliage. The photographs are of a two year old plant from cuttings grown in a 21-cm container. Photos were taken in August 2021 in Boskoop, The Netherlands. The colors shown are as true as can be reasonably obtained by conventional photographic procedures.

Figure 1:
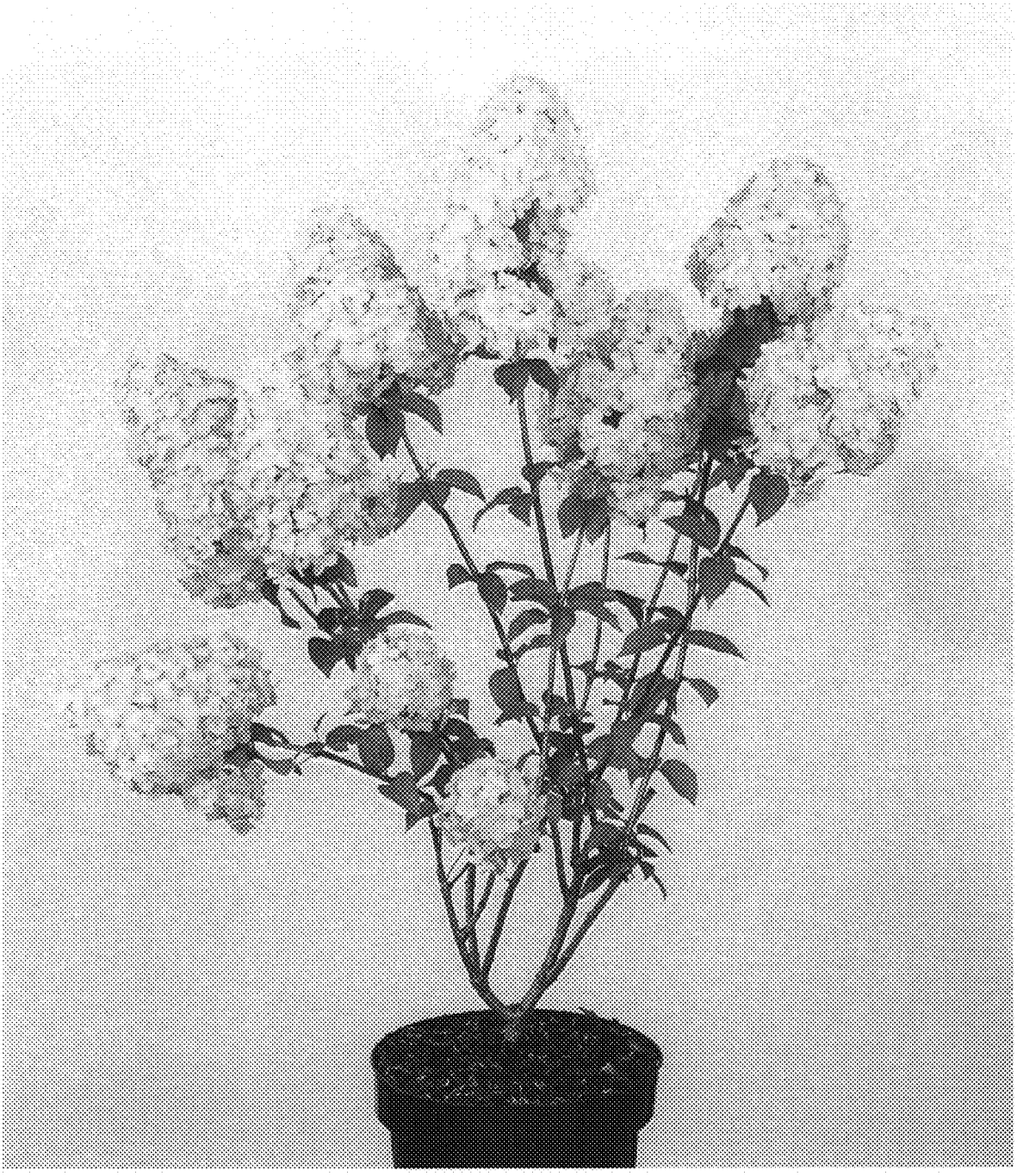
Figure 2:
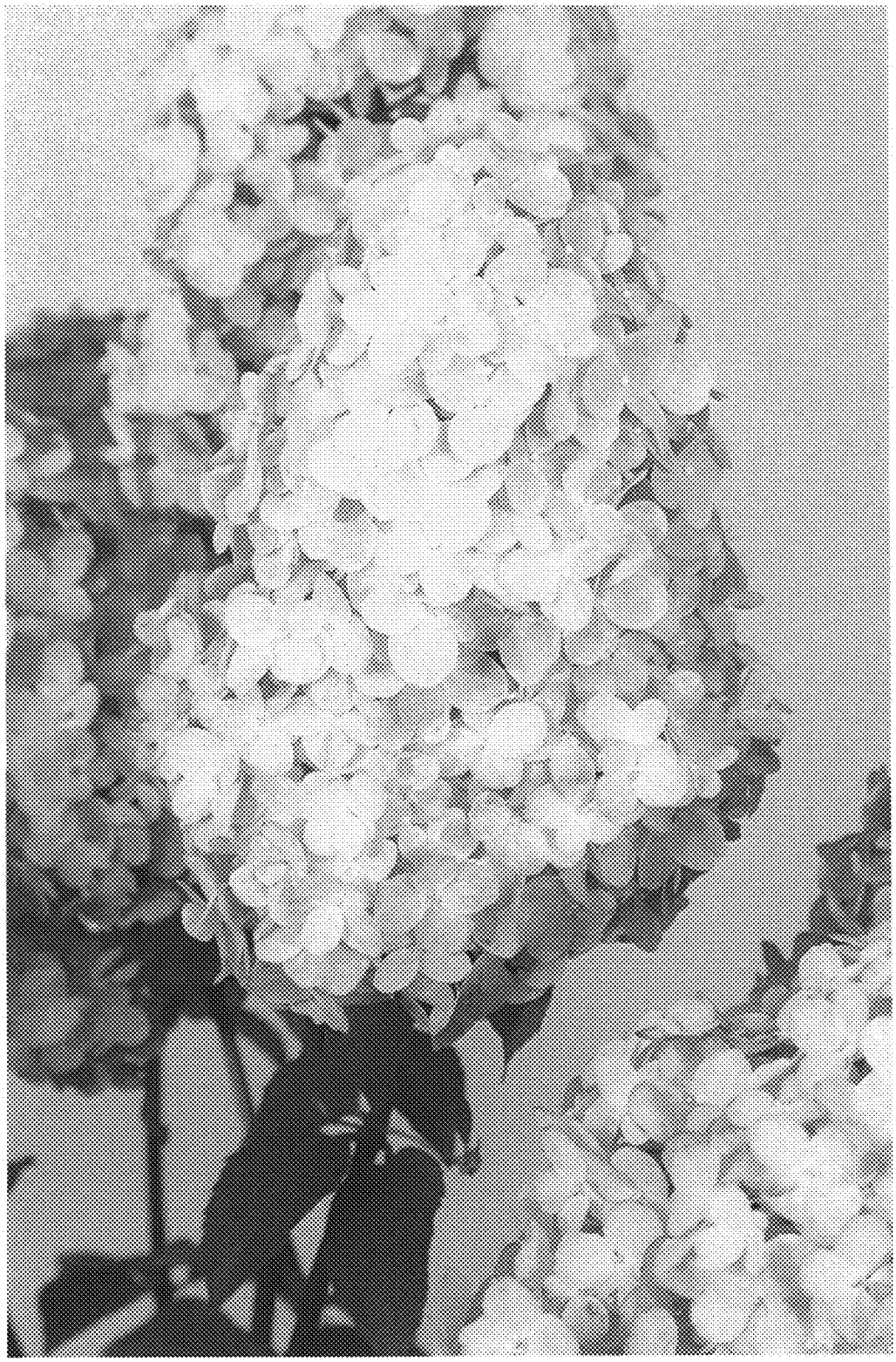
Figure 3:
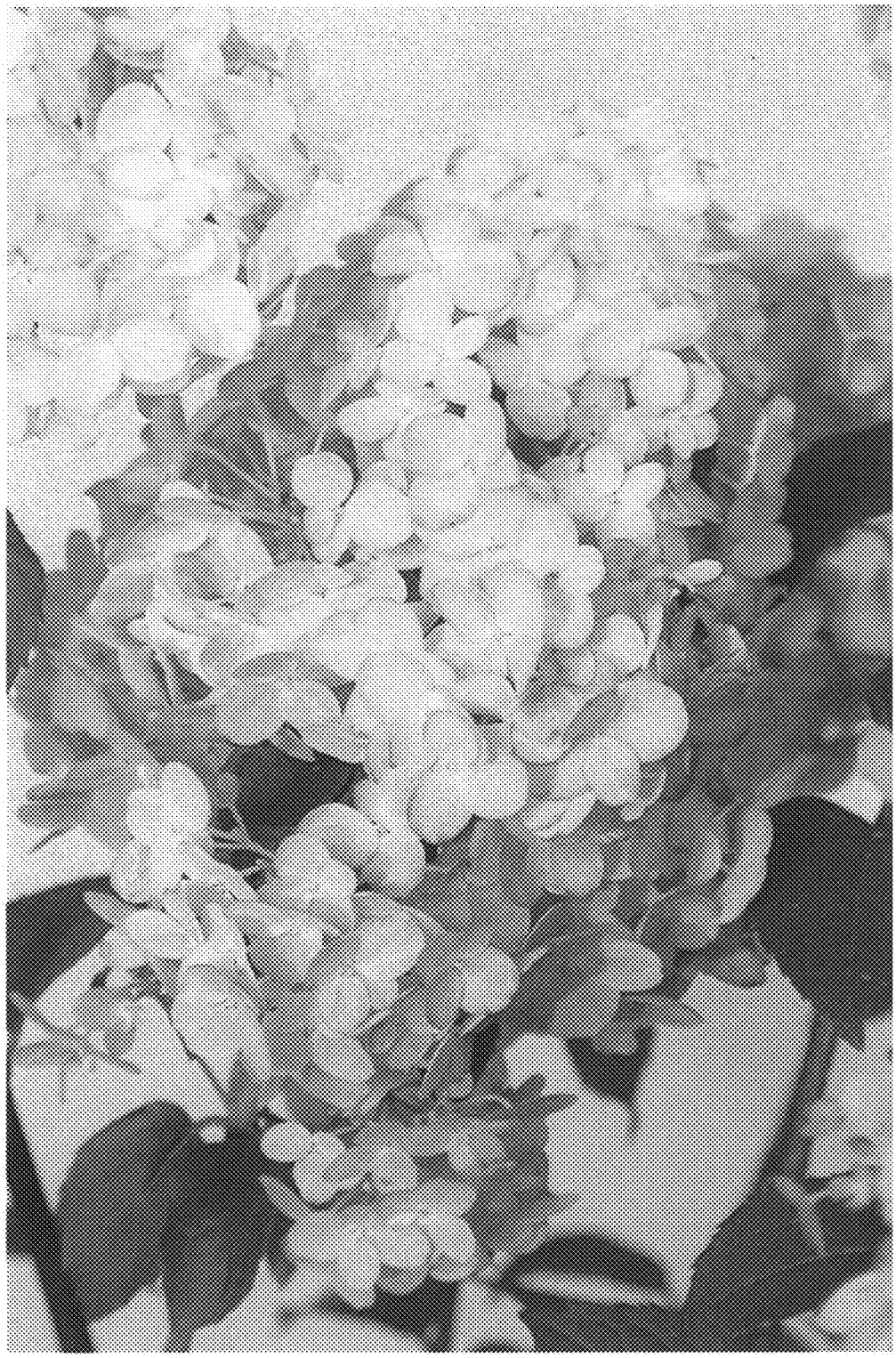

FIG. 1 shows the overall plant habit of 'COUHARIE'.
FIG. 2 shows a close-up of the flowers.
FIG. 3 shows a close-up of the inflorescence fading.

DESCRIPTION OF THE NEW VARIETY

The following detailed descriptions set forth the distinctive characteristics of 'COUHARIE'. The data which define these characteristics were collected from asexual reproductions carried out in Boskoop, The Netherlands. Data was collected on two-year old plants grown outdoors in 21 cm circular containers in Boskoop, The Netherlands in August 2021. The range of day temperatures was 16° C. to 30° C. and the range of night temperatures was 8° C. to 20° C. Color references are to The R.H.S. Colour Chart of The Royal Horticultural Society of London (R.H.S.), 6$^{th}$ edition (2015).

Classification:
- *Family.*—Hydrangeaceae.
- *Botanical.*—*Hydrangea paniculata.*
- *Common.*—*Hydrangea.*
- *Designation.*—'COUHARIE'.

Plant:
- *Propagation type.*—Vegetative cuttings.
- *Time to produce a finished plant.*—Average is twelve months from propagation to a small, finished plant.
- *Appropriate for what size of container.*—Field grown and in 13 in pots or larger.
- *Plant shape.*—Obovate.
- *Average plant height.*—76.9 cm.
- *Average plant diameter.*—77.5 cm.
- *Growth habit.*—Broad spreading-upright.
- *Growth rate.*—Moderate.
- *Vigor.*—Moderate to high.
- *Heat tolerance.*—At least tolerant to USDA Zone 9.
- *Cold tolerance.*—Tolerant to USDA Zone 5.
- *Tolerance to wind.*—Moderate.
- *Tolerance to rain.*—Moderate to high.

Branches:
- *Habit.*—Freely branching.
- *Basal branching.*—Present.

*Pinching*.—Not required but will improve branching.

*Lateral branches*.—Number of lateral branches per plant: Average of 17. Length: Average is 32.5 cm, excluding inflorescence. Diameter: Average is 0.5 cm. Internode length: Average is 7.4 cm. Appearance and shape: Rounded. Aspect/angle: Spreading-upright; average angle of 52.5 degrees to main branch. Strength: Strong. Color, immature: RHS 146D (Yellow-green). Color, mature: RHS N199B (Grey-brown) to RHS N199C (Grey-brown); Older bark RHS 197A (Greyed-green) and RHS 199A, RHS 199B and RHS N199B (Grey-brown). Pubescence: Not present. Lenticels: Stems sparsely covered with lenticels, average length 1.25 mm, average width 0.75 mm, colored RHS 164C (Greyed-orange); lenticels not visible on mature stems.

Foliage:

*Arrangement*.—Opposite or in whorls of three.

*Shape*.—Ovate.

*Apex*.—Apiculate.

*Base*.—Shallowly truncate to obtuse.

*Margin*.—Serrate.

*Length*.—Average is 5.6 cm.

*Width*.—Average is 3.5 cm.

*Texture*.—Upper surface: Smooth, glabrous. Lower surfaces: Smooth, glabrous, except for sparse pubescence on main vein and secondary veins.

*Pubescence*.—Under side sparsely pubescent on main vein and secondary veins with very short adpressed strigose hairs, average length: 0.5 mm, colored green-white; too small and too sparsely present to be measured with RHS-CC.

*Venation pattern*.—Pinnate.

*Venation color*.—Upper surface: RHS 146B and RHS 146C (Yellow-green). Lower surface: RHS 146D (Yellow-green).

*Color*.—Immature: Upper surface: RHS 137B (Green). Lower surface: RHS 146A to RHS 147B (Yellow-green). Mature: Upper surface: RHS 137A (Green). Lower surface: RHS 147B (Yellow-green).

*Petiole*.—Length: Average 0.6 cm. Diameter: Average is 1.75 mm. Color: Upper surface: RHS 146C (Yellow-green), with RHS 152A margins. Lower surface: RHS 146C to RHS 146D (Yellow-green). Texture: Upper surface: Slightly glossy, smooth and glabrous. Lower surface: Slightly glossy, sparsely covered with very short adpressed strigose hairs, average length: 0.4 mm, colored green-white; too small and too sparsely present to be measured with RHS-CC.

Flowers:

*Natural flowering season*.—Mid-summer to late summer.

*Time to flower*.—One season.

*Fragrance*.—Very faint, sweet and pleasant, typical *H. paniculata*-scent.

*Inflorescence type*.—Paniculate.

*Conspicuousness of the fertile flowers of the inflorescence*.—Weak.

*Panicle*.—Shape: Ovate to conical. Height: 18.0 cm. Diameter: 13.2 cm.

*Peduncle*.—Length: 11.1 cm. Diameter: 0.35 cm. Angle: Main peduncle straight on top of lateral branch (=0°), lateral peduncles in an average angle of 45.0° to main peduncle. Strength Moderately strong. Texture: Matte, sparsely covered with thin adpressed hairs; average length of hairs 0.4 mm, colored green-white, too small to be measured with RHS-CC. Color: RHS 147C (Yellow-green); sparsely to moderately covered with lenticels, average length: 1.0 mm, average diameter: 0.5 mm, colored RHS 145D (Yellow-green) to RHS 157A (Green-white).

*Sterile florets bud*.—Average length: 0.35 cm. Average diameter: 0.8 cm. Shape: Broad cup-shaped. Color: RHS 143C (Yellow-green).

*Fertile florets bud*.—Average length: 0.25 cm. Average diameter: 0.20 cm. Shape: Broad ovate. Color: RHS NN155D (White), base is RHS 145C to RHS 145D (Yellow-green).

*Sterile florets*.—Persistent with an average of 650 of sterile florets per inflorescence. Aspect: Upright and outward to slightly drooping. Shape: Rotate. Average diameter: 2.4 cm. Average depth: 0.6 cm. Longevity of florets on plant is 6 weeks. Petals: Number per floret: 4, occasionally 5. Arrangement: Rotate. Shape: Ovate, concave. Tip: Acute. Base: Cuneate. Margin: Entire. Length: 0.2 cm. Width: 0.1 cm. Texture: Upper surface: Glabrous, slightly glossy. Lower surface: Glabrous and matte. Color when opening: Upper surface: RHS NN155D (White). Lower surface: RHS NN155D (White), top tinged RHS 75C (Purple). Color full open: Upper surface: RHS NN155D (White).. Lower surface: RHS NN155D (White), top tinged RHS 75C (Purple).

*Sepals*.—Average number: 4 or occasionally 5 per floret. Arrangement: Rotate. Shape: Ovate to elliptic. Apex: Shallowly retuse to obtuse. Base: Cuneate. Margin: Entire. Length: 1.3 cm. Width: 1.2 cm. Texture (both surfaces): Glabrous and matte. Color: When opening: Upper surface: RHS 145B (Yellow-green) and flushed lighter RHS 145C (Yellow-green). Lower surface: RHS 145C (Yellow-green). Fully opened: Upper surface: RHS 150D (Yellow-green). Lower surface: Blend of RHS 145D and RHS 150D (Yellow-green). Fading to: Upper surface: RHS 150C (Yellow-green), strongly flushed with RHS 185C and RHS 185D (Greyed-purple). Lower surface: RHS 145D and RHS 150D (Yellow-green), moderately to strongly flushed with RHS 185C and RHS 185D (Greyed-purple).

*Pedicel*.—Length: 1.5 cm. Diameter: 0.1 cm. Angle: 22.5 degrees to main peduncle. Strength: Moderately strong. Texture: Matte, very sparsely covered with thin adpressed hairs; average length of hairs: 0.4 mm, colored green-white; too small and too sparsely present to be measured with RHS-CC. Color: RHS 157B (Green-white).

Fertile flowers:

*Number of fertile flowers per inflorescence*.—360.

*Aspect*.—Upright.

*Shape*.—Rotate, petals drop when maturing.

*Diameter*.—0.7 cm.

*Depth*.—0.35 cm.

*Flower longevity*.—Five days.

*Persistent or self-cleaning*.—Self-cleaning.

*Petals*.—Petals per flower: 5. Arrangement: Rotate. Shape: Ovate, moderately concave. Tip: Acute. Base: Cuneate. Margin: Entire. Length: 0.25 cm. Width: 0.15 cm. Texture: Upper surface: Glabrous, slightly glossy. Lower surface: Glabrous matte. Color when opening: Upper surface: RHS NN155D (White). Lower surface: RHS NN155D (White), tinged RHS 75C (Purple). Color fully open: Upper surface: RHS NN155D (White). Lower surface: RHS NN155D (White), top slightly tinged RHS 75C to RHS 75D (Purple).

*Sepals*.—Number: 5. Arrangement: Rotate. Shape: Deltoid. Tip: Broad acuminate. Base: Broad cuneate. Margin: Entire. Length: 0.1 cm. Width: 0.1 cm. Texture: Upper surface: Glabrous matte. Lower surface: Glabrous, very slightly matte. Color when opening: Upper surface: RHS 145D (Yellow-green). Lower surface: RHS 145D (Yellow-green). Color fully open: Upper surface: RHS 145D (Yellow-green). Lower surface: RHS 145D (Yellow-green).

*Pedicel*.—Length: 0.2 cm. Diameter: 0.05 cm. Angle: 20 degrees to main peduncle. Strength: Moderate. Texture: Matte, moderately to densely covered with a thin pubescence; average length of hairs: 0.3 mm, colored white to green-white; too small and too sparsely present to be measured with RHS-CC. Color: RHS 145D (Yellow-green) to RHS 157B (Green-white).

Reproductive organs:

*Sterile flowers*.—Androecium: Present. Stamens: 8. Filament length: 0.2 cm. Filament color: RHS NN155D (White). Anther shape: Broad oblong. Anther length: 0.04 cm. Anther color: RHS 151C (Yellow-green). Pollen amount: Low. Pollen color: RHS 156B (Greyed-white). Gynoecium: Absent.

*Fertile flowers*.—Stamens: 10. Filament length: 0.3 cm. Filament color: RHS NN155D (White). Anther shape: Broad oblong. Anther length: 0.3 cm. Anther color: RHS 153D (Yellow-green). Pollen amount: Low to moderate. Pollen color: RHS 156B (Greyed-white). Pistils: 3. Pistil length: 0.075 cm. Stigma shape: Club-shaped. Stigma color: RHS 157D (Green-white). Style length: 0.1 cm. Style color: RHS 157D (Green-white). Ovary color: RHS 145D (Yellow-green) and RHS 157A (Green-white).

Seed: Not observed.

Disease and pest resistance: The disease which are occur in *H. paniculata* and also in 'COUHARIE' are: white fly, black spots, powdering mildew, lice.

COMPARISON WITH PARENTAL VARIETIES

The parental lines for 'COUHARIE' are unknown so no comparison information is available.

COMPARISON TO KNOWN VARIETY

'COUHARIE' is most similar to the commercial *Hydrangea* plant named 'AJ14' (U.S. Plant Pat. No. 30,983). Differences between the two varieties are described in Table 1:

TABLE 1

Comparison with Similar Variety

| Characteristic | Variety 'COUHARIE' | Commercial line 'AJ14' |
|---|---|---|
| Plant Shape | Obovate | Broad obovate to near globular |
| Growth rate | Moderate | Low to moderate |
| Vigor | Moderate to high | Moderate |

I claim:

1. A new and distinct cultivar of *Hydrangea* Plant Named 'COUHARIE' as described and illustrated herein.

* * * * *